United States Patent [19]

Slemeyer

[11] Patent Number: 4,459,994

[45] Date of Patent: Jul. 17, 1984

[54] METHOD FOR ASSURING VALID MEASURED VALUES OF BREATH ALCOHOL CONCENTRATION

[75] Inventor: Andreas Slemeyer, Karlsruhe, Fed. Rep. of Germany

[73] Assignee: Siemens Aktiengesellschaft, Berlin and Munich, Fed. Rep. of Germany

[21] Appl. No.: 391,142

[22] Filed: Jun. 23, 1982

[51] Int. Cl.³ .............................................. A61B 5/00
[52] U.S. Cl. ................................................. 128/719
[58] Field of Search ...................... 128/633, 664, 719; 73/19, 23

[56] References Cited

U.S. PATENT DOCUMENTS

| 4,140,106 | 2/1979 | Kirmaier | 128/719 |
| 4,314,564 | 2/1982 | Albarda | 128/719 |
| 4,316,380 | 2/1982 | Heim et al. | 128/719 X |

FOREIGN PATENT DOCUMENTS 2746078  4/1979  Fed. Rep. of Germany ...... 128/719

Primary Examiner—Kyle L. Howell
Assistant Examiner—Francis J. Jaworski
Attorney, Agent, or Firm—Karl F. Milde, Jr.; Andrew G. Rodau

[57] ABSTRACT

A method for assuring valid measured values of breath alcohol concentration for the determination of the alcohol concentration in human blood by means of a gas analyzer operating on the principle of infrared absorption. Values of the rise of expiration concentration S(t) independent of the vital capacity of the subject, that is, the maximum expiration volume after deep inhalation, are calculated from the measured values of the breath alcohol concentration and expiration volume and subjected to a criterion comprising positive and negative threshold values (trigger levels) before they are released for further processing.

The giving out of invalid measured values, which are attributable to too low an expiration volume, too short an expiration time, residual alcohol in the mouth or insufficient sample volume, is avoided.

4 Claims, 7 Drawing Figures

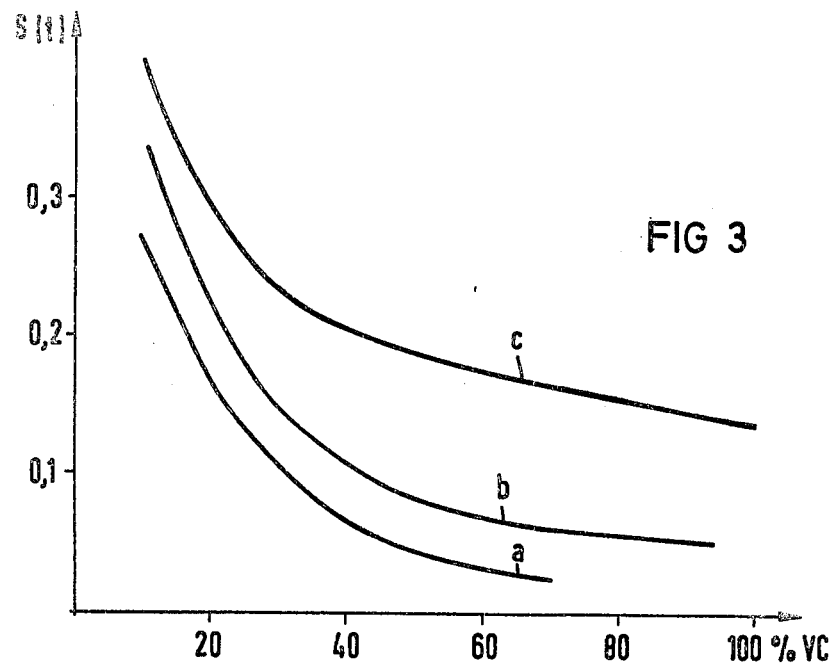
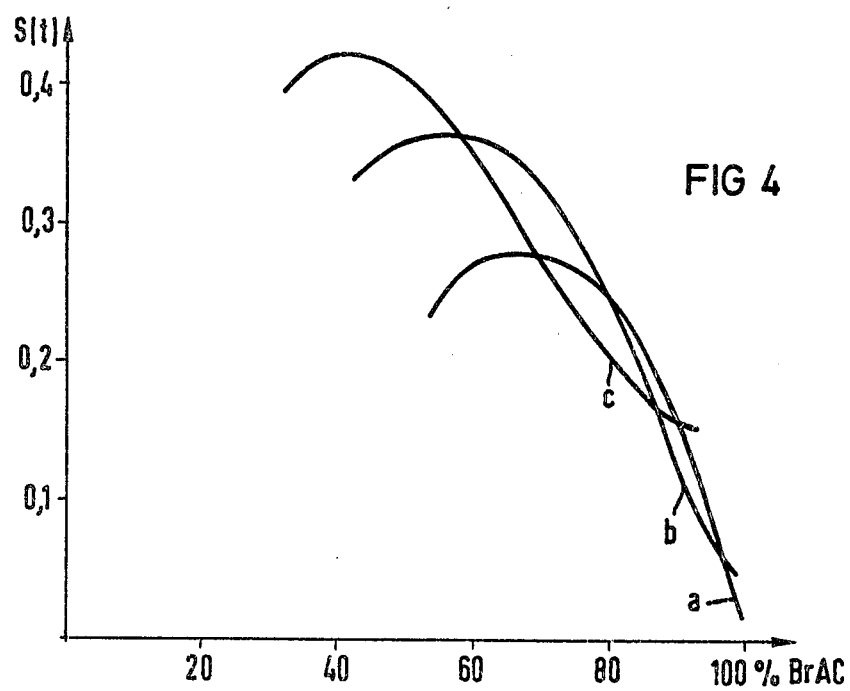

METHOD FOR ASSURING VALID MEASURED VALUES OF BREATH ALCOHOL CONCENTRATION

BACKGROUND OF THE INVENTION

1. Field of the Invention

The invention relates to a method for assuring valid breath samples for determining alcohol concentration in the blood by analysis of the alcohol concentration in alveolar expiration air.

2. Description of the Prior Art

The basis of all measuring methods which determine the blood alcohol concentration (BAC) through the analysis of the breath alcohol concentration (BrAC) is the assumption that a constant relationship exists between the alcohol concentration of the blood and that of the expiration air. This, however, is true only for those portions of the expiration air which are in equilibrium with the alveolar concentration. For a correct determination of the BAC from the analysis of the BrAC, therefore, it must be regarded as a necessary prerequisite that a breath sample is furnished which in the final expiratory phase consists predominantly of alveolar air. By approximation this can be established with reference to the time response of the expiration concentration by the fact that the latter shows a recognizable plateau formation toward the end of expiration.

This is what a number of methods are based on which determine the time response of the concentration rise and which acknowledge the furnished breath sample as valid when it falls below a threshold value (see, for example, U.S. Pat. No. 4,090,078). This, however, still requires that an uninterrupted minimum air volume flow be furnished over a minimum time period in order to provide the required minimum total volume for analysis. There is thus a purely logical relationship between increase in measured concentration and the minimum volume which does not take into consideration the physical make-up of the subject. In order that a valid measurement can also be made for persons with a low vital capacity (VC), the minimum volume or minimum volume flow must not be set too high. Persons with great vital capacity are thus able, by reducing their volume flow to the required minimum, to diminish the concentration increase as a function of time to the extent that it falls below the threshold value although there would still be a considerable residual lung volume. In this case the breath sample used for analysis would clearly lie below the alveolar equilibrium concentration and would suggest a lower alcoholization.

The effect of ventilation (breathing) before furnishing the sample on the response of the eliminated breath alcohol concentration is illustrated in FIG. 1. Curve a describes the concentration increase as it would result after normal inhalation before the test. After a steep initial rise, the curve flattens after a few seconds and merges with the asymptotic limit line which corresponds to the alveolar equilibrium concentration. If before the sample is taken the breathing is interrupted for several seconds, a steeper rise and hence a faster approach to the equilibrium concentration is brought about, as shown by curve b.

The contrary occurs in the case of forced ventilation or hyperventilation before the test. Compared with normal breathing, curve c shows a much greater rise in the final expiratory phase, the fact being that the actual value of the BrAC can no longer be reached even after a minimum time (e.g. 4 seconds) has been exceeded. Also, under hyperventilation the concentration increase in time can be diminished by reduction of the throughput of respiratory air to such an extent that the required threshold value for a valid breath sample is reached.

All of the identified interfering factors, such as insufficient sample volume or hyperventilation, lead in principle to an underestimation of the breath alcohol concentration. This is not so in the presence of residual alcohol in the mouth. This may be the case if the time between end of drinking and test is less than 15 minutes. By measuring there would result a curve according to FIG. 2, which is marked by a strong overshoot. Even toward the end of expiration, the influence of residual alcohol in the mouth may be so strong that a value far above the actual breath alcohol concentration is simulated. The same is true for air which, having been brought up from the stomach by belching, mixes with the expiration air. Measuring techniques should make it possible to identify and eliminate resulting erroneous evaluations of the degree of alcoholization.

Studies prior to the invention have shown that the most important factor influencing the concentration rise during the expiration phase lies in the preceding inspiration volume. At uniform exhalation there is then found a quasi-linear dependence between inspiration depth and rise. This is due to exchange processes of ethanol in the supplying respiratory tracts. The inhalation of alcohol-free air leads at first to a strong reduction of the surface concentration, which can be cancelled out essentially only by letting the same volume of alcohol-saturated alveolar air stream pass again during exhalation. In so doing, alcohol is drawn from the expiration air until the concentration equilibrium in the supplying respiratory tracts is restored. Doubling the inhalation volume thus requires also a doubling of the exhalation volume, so as to initiate a plateau formation in the concentration curve toward the end of expiration.

It can further be seen from the investigations that for equal inspiration and expiration volumes, on the average only 80% of the alveolar equilibrium concentration values are reached, and for this reason additional expiration volume must be demanded of the subject. The latter, however, is able to supply this only if he has inhaled not more than approximately 40% of his vital capacity. The additionally needed volume will become greater, moreover, with increasing volume of the measuring chamber of the analyzer. For this reason the chamber must be made as small as possible.

It is evident from the foregoing that fulfillment of the minimum volume condition is usable for persons having comparable vital capacity only if in addition the same inhalation depth exists. The same applies to the control of the concentration increase in time. Information about the approximation to the equilibrium concentration can be derived from it only if the furnished volume flow has a certain ratio to the vital capacity of the subject. To establish that a valid sample has been furnished, it would therefore be necessary to measure both the vital capacity and the inspiration and expiration volume. In practice, this is hardly possible with the means available in the prior art. Knowledge about the above-named relationships was therefore not previously usable to eliminate invalid samples from the evaluation of the actual degree of alcoholization.

SUMMARY OF THE INVENTION

It is an object of the invention to provide practical breath alcohol content measuring techniques that overcome the problems of inaccuracy of prior art breath sampling techniques discussed above.

According to the invention, information about the degree of approximation to the equilibrium concentration is to be derived from analysis of only the expiration and by means of simple calculations. The invention makes use of the finding that the volume variation-related gradient S(t) of the expiration concentration can be used as the sole decision parameter for alcohol content determination, using the relationship:

$$S(t) = \frac{\frac{d\,BrAC(t)}{dt}}{\frac{d\,V(t)}{dt}} \cdot \frac{V(t)}{BrAC(t)} = \frac{d\,BrAC(t)}{d\,V(t)} \cdot \frac{V(t)}{BrAC(t)} \quad (1)$$

where V(t)=expired sample volume

The term V(t)/BrAC(t) is a normalization factor which serves to make S(t) independent of the magnitude of the breath alcohol concentration BrAC and of the quantity of the expiration volume V. This equation, therefore, relates the percentage concentration variation to the percentage volume variation. The relationship has the added advantage that it applies independently of the actual vital capacity of the subject.

BRIEF DESCRIPTION OF THE DRAWINGS

The invention is explained in more detail below with reference to the embodiments illustrated in FIGS. 1-7 of the drawings in which:

FIG. 3 is a graphical representation of the response of the volume-related gradient S(t) as a function of the expiration volume, the inspiration volume forming the parameters;

FIG. 4 is a graphical representation of the relationship of FIG. 3, but plotted with respect to the breath alcohol concentration BrAC;

DESCRIPTION OF THE PREFERRED EMBODIMENT

Figure 1:
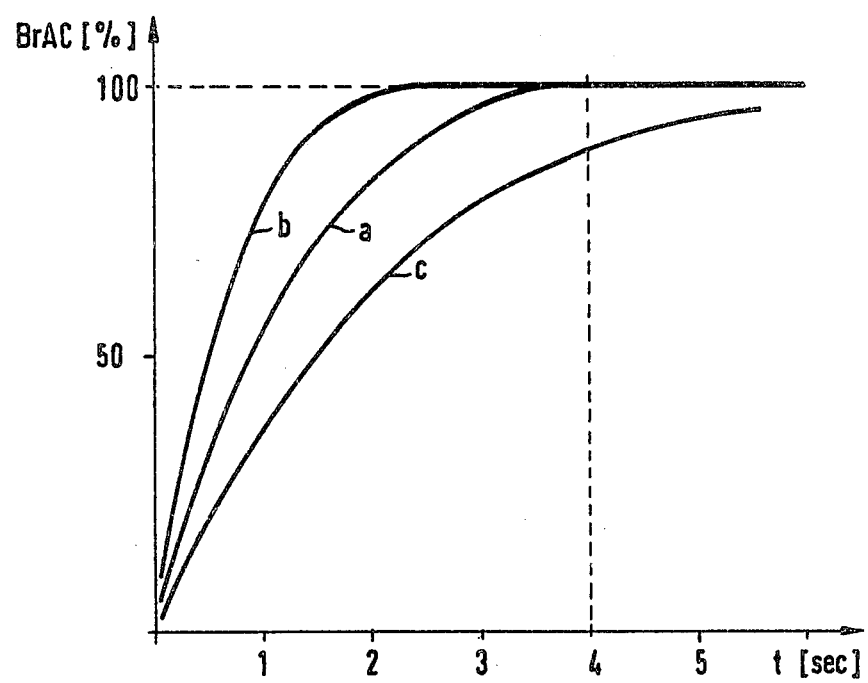
FIG. 1 is a graphical representation (discussed above) of the time dependence of alcohol concentration in the respiratory air as a function of ventilation before the test.
Figure 2:
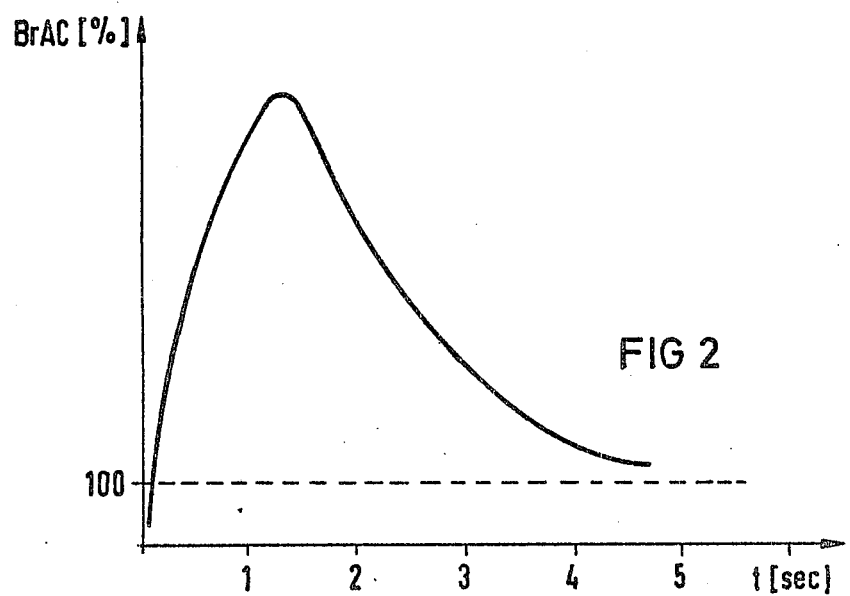
FIG. 2 is a graphical representation (discussed above) of the alcohol concentration response when residual alcohol is present in the mouth.

Considering the expiration concentration as the sole decision parameter for determining blood alcohol concentration, the following observation is made: when breath alcohol concentration is plotted graphically against relative vital capacity, it is found that for a particular given relative inspiration volume the rise response is independent of both the breath flow velocity and the actual vital capacity of the test subject. This relationship is illustrated in FIG. 3. The parameter is the relative inspiration volume referred to the vital capacity VC. Curve a applies to 20% VC, curves b and c to 40 and 100% VC, respectively. In the two first-named cases, the curves end at 70 and 90% of the VC, respectively, corresponding to the sum of inspiration volume and reserve volume. Curve c was preceded by a complete expiration and inspiration (forced ventilation). With increasing inspiration volume the value of the rise S in the final expiratory phase increases, because the exchange processes in the respiratory tracts are not yet fully completed.

From the rise response in dependence on the eliminated BrAC an unambiguous correlation can be derived between the magnitude of S and the approximation to the alveolar equilibrium concentration. Thus, for example, 90% of the actual BrAC is reached or exceeded only if the condition $S \leq 0.15$ is fulfilled (curves a and b in FIG. 4). At incomplete sampling or forced ventilation, however, this is not possible.

A special advantage of the method according to the invention is that the degree of approximation to the alveolar equilibrium concentration can be determined independently of inspiration volume and vital capacity from the magnitude of the rise S. Comparison of the magnitude S with a threshold value furnishes information as to whether additional volume must be exhaled for a correct determination of the breath alcohol concentration to be carried out.

A further application of this rise criterion results in the case of residual alcohol in the mouth. Here much higher concentration values occur briefly at the beginning of expiration than subsequently. This results in the calculation of negative values for the quantity S from which such a situation can be recognized with certainty by measurement. Hence the following threshold values can be defined:

(a) Positive Threshold Value S+: Reaching or falling short of this value signals that the furnished breath sample has sufficiently approached alveolar equilibrium concentration, and can therefore be acknowledged as valid. The alcohol concentration measured at this moment is immediately supplied to the display, and the measuring process is ended. Optionally, it is possible to also await the moment when the difference of two sampled (sensed) values of V has dropped below the threshold value again, to obtain the possibly still existing residual volume for the sample.

(b) Negative Threshold Value S−: If this value is exceeded, the measuring process is stopped, and a reference is made to residual alcohol in the mouth.

The exact value of the magnitude of the Positive Threshold Value S+ depends on what accuracy the apparatus used permits and what accuracy is demanded by the legal regulations. The Positive Value S+ should be chosen so that it is reached when the actual BrAC has approached its end value to the extent that measuring accuracy permits and the legal regulations demand. As a practical matter, S+ can be selected so that the threshold value is reached when the actual BrAC has approached to within about 5% of its end value. This means that S+ should be between +0.2 and +0.1 and preferably between +0.15 and +0.1.

The Negative Threshold Value S− should be between −0.2 and −0.3, with a preferable value being −0.3. The value of S− should be selected so that it is not reached for low amounts of residual alcohol in the mouth.

The application of the method of the invention is explained with reference to three examples, shown graphically in FIG. 5. The ordinate of the graph is divided for convenience into the following zones:

Zone I: $0 < S(t) \leq S+$
Zone II: $S(t) > S+$
Zone III: $S(t) < S-$

The transitions between the zones are marked by the threshold values $S+$ and $S-$.

Figure 5:
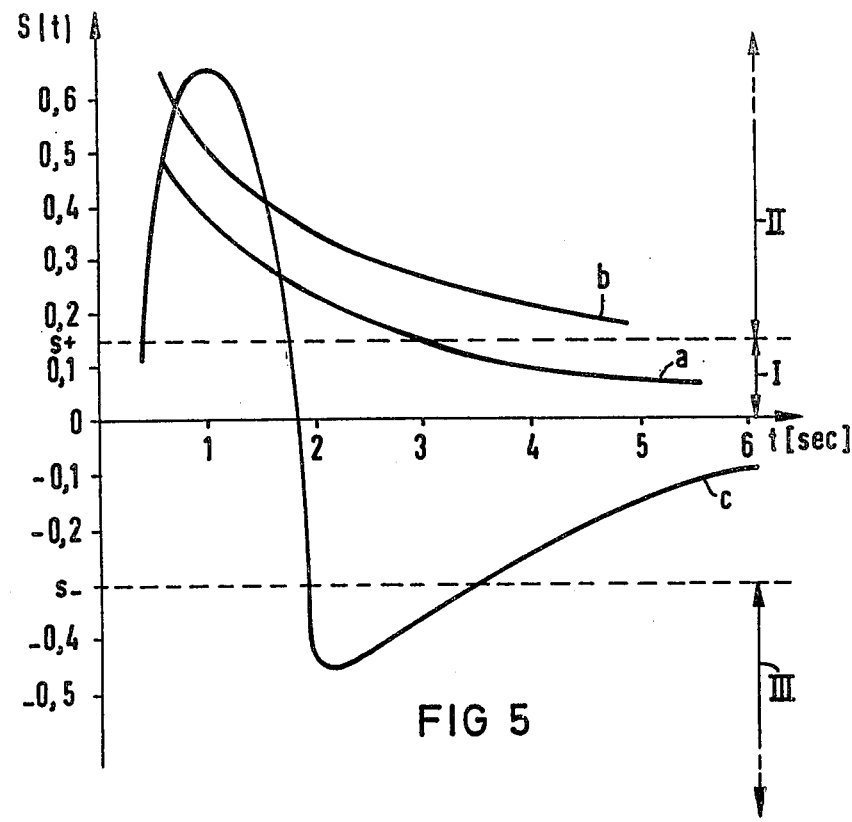
FIG. 5 is a graphical representation of examples for the application of the rise criterion by means of various threshold values.

At normal ventilation before the test, the magnitude S(t) decreases steadily in the course of expiration, until finally it changes over from Zone II to Zone I, remaining there to the end of exhalation (curve a of FIG. 5). As soon as the value falls below the threshold value $S+$, the breath sample is regarded as valid. Taking $S+ = 0.15$, this would already occur after three seconds. Alternatively, the end of expiration may be awaited, which is marked by a decrease below a minimum respiratory air throughput.

Curve b of FIG. 5 illustrates a breath sample characteristic of either disturbances of the exchange processes before the test or of an insufficient sample volume. The latter could be determined from the measured value of the expiration volume. Since for curve b, the value of S(t) remains in zone II during the entire process, the measurement is considered invalid and should be repeated.

Curve c of FIG. 5 is illustrative of a breath sample for which the volume-related rise is influenced by residual alcohol in the mouth. The curve of such a breath sample is characterized by sweeping of the zones in the sequence II, I and III. As soon as the value has fallen below the threshold value $S-$ (e.g. $S- = -0.3$), further measurement can be stopped, since under those circumstances no physiologically relevant results can be obtained. Residual alcohol in the mouth can also be detected by forming the time derivation of S(t). If the derivative passes through two zero positions in conjunction with a change of sign, interference by residual alcohol in the mouth may be inferred.

Figure 6:
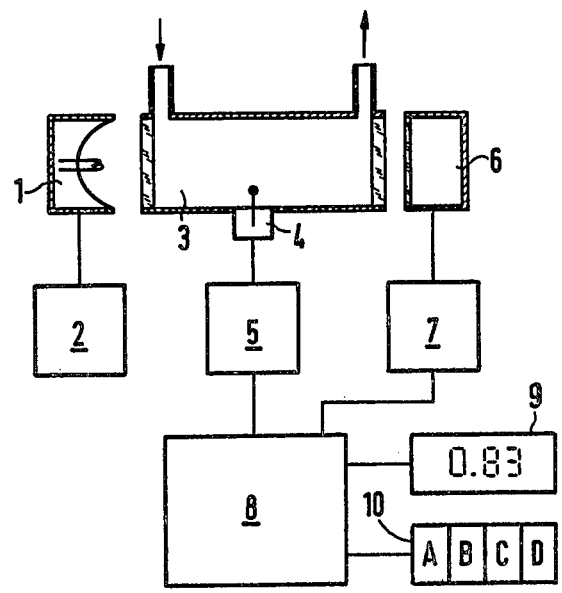
FIG. 6 is a schematic circuit diagram of an embodiment of apparatus used for the practice of the method.

FIG. 6 shows an embodiment of a measuring device for the practice of the method. The device operates on the principle of non-dispersive infrared absorption. Radiation emitted by an infrared radiator 1 and modulated mechanically or electronically passes through an analytical cell 3 of small volume charged with exhaled air and impinges on the exit side on a selective infrared receiver 6. The receiver 6 may, for example, be an opto-pneumatic detector or a combination of an interference filter and a photo-resistor.

Determination of the expiration volume is performed by a flow sensor 4 which is disposed in the flow path, and preferably functions on the hot wire anemometer principle. The signals of the flow sensor 4 and of the infrared receiver 6 are processed in connected electronic modules 5 and 7 in the manner described further below, in such a way that they can be processed by a computer 8, e.g. a micro-processor.

The results of the analysis are communicated to the test operator by means of a display or printer unit 9. In addition display fields 10 are provided for interference messages A, B, C and D.

To calculate the rise S(t) according to the formula (1) given above, the differential quotients of BrAC(t) or respectively V(t) are replaced by difference quotients which result from the sampling (scanning) of the input values in short intervals of time.

The application of the volume-related rise criterion presupposes a fulfillment of physiological limit conditions.

Figure 7:
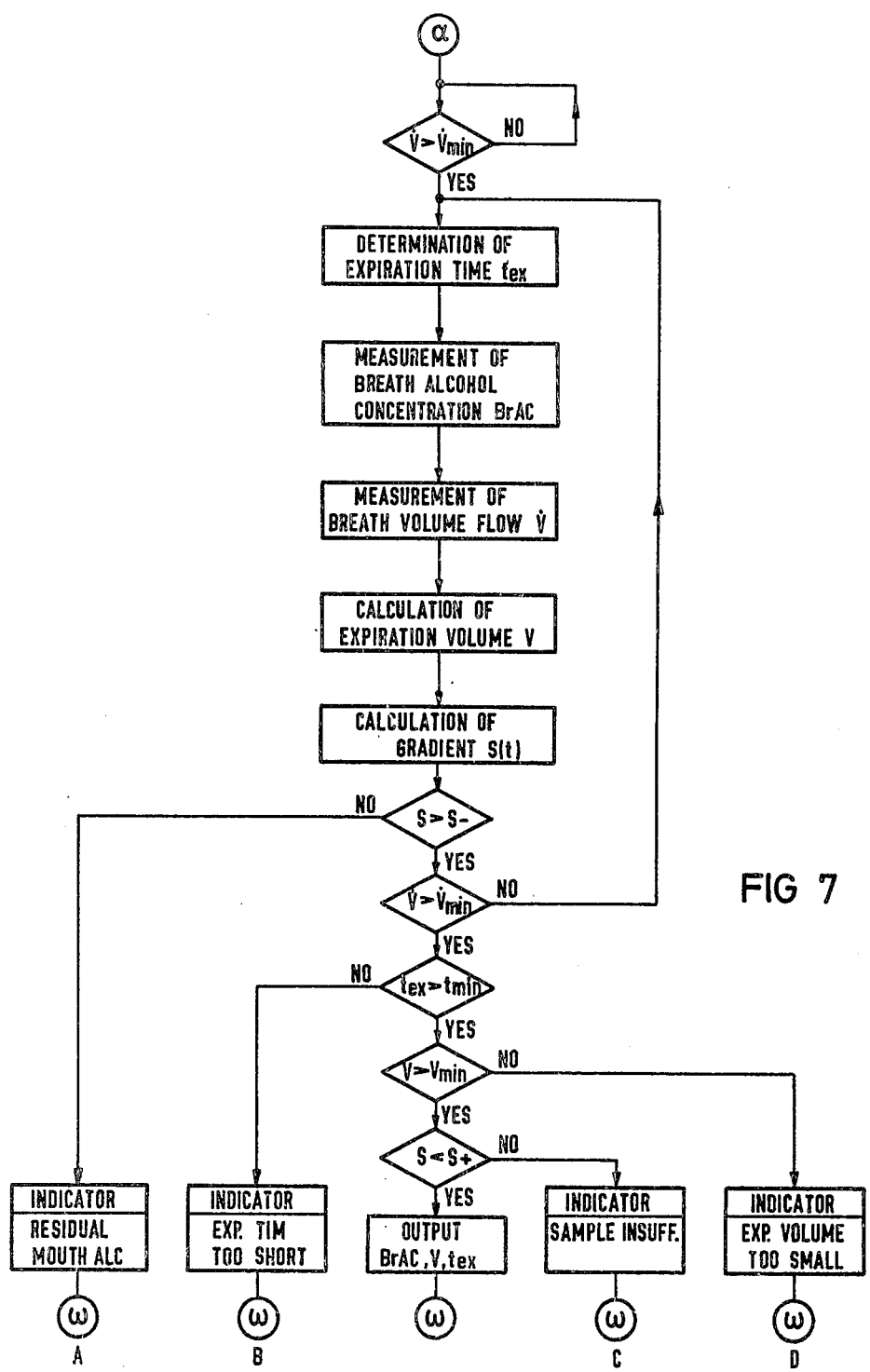
FIG. 7 is a flow diagram of the process steps occurring in the circuit arrangement of FIG. 6.

The sequencing of process steps performed by the circuit arrangement of FIG. 6 is shown by the flow diagram of FIG. 7.

The beginning of a sample delivery is established when the breath volume flow $\dot{V}$ exceeds a given threshold value $V_{min}$ (critical flow). The measurement is terminated when the flow falls below this threshold value again for the first time, as is the case both at the end of expiration and also upon arbitrary interruption of the breathing. During the time that the breath volume flow $\dot{V}$ exceeds the threshold $V_{min}$, called $t_{ex}$, a continuous evaluation of the input data as well as the calculation of the rise S(t) is performed. If values occur which are smaller than the negative threshold value $S-$, the evaluation is terminated, and an error message tells the test operator that residual alcohol in the mouth is indicated.

The sequence of the remaining criteria corresponds to their physiological value. First, a determination is made as to whether $t_{ex}$ is greater than an instrument-related minimum time. If so, a determination is made whether a minimum volume $V_{min}$ related to the capacity of the instrument has been expired. Only then can a meaningful evaluation of S be undertaken. If S is smaller than the positive threshold value $S+$, the measured BrAC value as well as other quantities of interest, such as V, $t_{ex}$ and S are released for display or printing. Otherwise, the reason for rejection of a sample is exhibited, i.e. the respective violated condition is named.

The invention thus makes it possible for the subject to modify his breathing accordingly and thus to contribute to a correct evaluation.

Having thus described the invention with particular reference to the preferred forms thereof, it will be apparent to those skilled in the art to which the invention pertains, after understanding the invention, that various changes and modifications may be made therein without departing from the spirit and scope of the invention as defined by the claims appended hereto. It will be appreciated that the selection, connection and layout of the various components of the described configurations may be varied to suit individual tastes and requirements.

What is claimed is:

1. A method for ascertaining valid breath samples for determining the blood alcohol concentration BAC by analysis of the alcohol concentration in alveolar expiration air, characterized in the steps of:

(a) measuring the expiration volume V(t) per unit of time;
    (b) measuring the breath alcohol concentration BrAC(t);
    (c) calculating therefrom the gradient S(t) of the expiration concentration, according to the formula $$S(t) = \frac{d\,BrAC(t)}{d\,V(t)} \times \frac{V(t)}{BrAC(t)} \; ; \text{ and}$$

(d) making use of the measured value of BrAC for further evaluation of blood alcohol BAC, if S(t) lies between a positive threshold value $S+$ and a negative threshold value $S-$, $S+$ being present when S(t) approximates its final value, according to alveolar equilibrium concentration, and $S-$ being present when S(t) is less than or equal to 0.

2. A method according to claim 1, characterized in that $S+$ is present when the actual BrAC has approached to within 5% of its end value.

3. A method according to claim 1, characterized in that $S+$ has a value between $+0.2$ and $+0.1$.

4. A method according to any one of claims 1 to 3, characterized in that $S-$ has a value of $-0.3$.

* * * * *